US00PP27906P3

(12) United States Plant Patent
Klemm et al.

(10) Patent No.: US PP27,906 P3
(45) Date of Patent: Apr. 18, 2017

(54) ***DIANTHUS* PLANT NAMED 'KLEDP14216'**

(50) Latin Name: *Dianthus caryophyllus*
Varietal Denomination: KLEDP14216

(71) Applicant: Klemm+Sohn GmbH & Co. KG, Stuttgart (DE)

(72) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 72 days.

(21) Appl. No.: 14/545,535

(22) Filed: May 18, 2015

(65) Prior Publication Data

US 2016/0014947 P1 Jan. 14, 2016

Related U.S. Application Data

(60) Provisional application No. 61/998,890, filed on Jul. 10, 2014.

(51) Int. Cl.
*A01H 5/02* (2006.01)

(52) U.S. Cl.
USPC ..... Plt./278

(58) Field of Classification Search
USPC ..... Plt./278
See application file for complete search history.

*Primary Examiner* — Anne Grunberg
(74) *Attorney, Agent, or Firm* — Barbara Campbell; Bethany R. Roahrig; Cochran Freund & Young, LLC

(57) ABSTRACT

A new variety of *Dianthus* plant designated 'KLEDP14216' having purple and dark-red double flowers and a mainly upright plant habit with little drooping, is disclosed.

1 Drawing Sheet

Genus and species: *Dianthus caryophyllus*.
Variety denomination: 'KLEDP14216'.

BACKGROUND

The present invention comprises a new and distinct variety of *Dianthus*, botanically known as *Dianthus caryophyllus*, and hereinafter referred to by the variety name 'KLEDP14216'. 'KLEDP14216' originated from a cross-pollination between the proprietary female *Dianthus* parent 'DCP 2006 0122' (unpatented) and the proprietary male *Dianthus* parent 'DCP 2007 0092' (unpatented) in May 2008 in Stuttgart, Germany.

The seeds from the cross were sown and plants were grown in a greenhouse for evaluation, where an individual plant designated 'KLEDP14216' was selected from the group of plants in May 2009 in Stuttgart, Germany. In October 2009, 'KLEDP14216' was first vegetatively propagated by vegetative cuttings. 'KLEDP14216' was found to reproduce true to type in successive generations of asexual propagation in Stuttgart, Germany via vegetative stem cuttings.

SUMMARY

The following are the most outstanding and distinguishing characteristics of this new variety when grown under normal horticultural practices in Stuttgart, Germany.

1. Purple and dark-red double flowers; and
2. A little hanging character but first upright, stems and flower stems are more hanging from beginning of the flowering.

DESCRIPTION OF THE PHOTOGRAPH

This new *Dianthus* plant is illustrated by the accompanying photograph of a plant approximately 10 to 12-weeks old and grown in a glass greenhouse in Stuttgart, Germany.

The colors shown are as true as can be reasonably obtained by conventional photographic procedures.

The photograph shows the whole plant habit, including flowers, foliage, and buds of 'KLEDP14216' taken in April 2012.

DESCRIPTION

The following detailed descriptions set forth the distinctive characteristics of 'KLEDP14216'. The data which define these characteristics were collected from asexual reproductions carried out in Stuttgart, Germany. Data was collected on 5-month old plants grown in a greenhouse in May 2014. Color references are to The R.H.S. Colour Chart of The Royal Horticultural Society of London (R.H.S.), 5$^{th}$ edition (2007).

Classification:
- *Family*.—Caryophyllaceae.
- *Botanical*.—*Dianthus caryophyllus*.
- *Common*.—Pot carnation.
- *Designation*.—'KLEDP14216'.

Parentage:
- *Female parent*.—The proprietary *Dianthus* variety 'DCP 2006 0122' (unpatented).
- *Male parent*.—The proprietary *Dianthus* variety 'DCP 2007 0092' (unpatented).

Plant:
- *Propagation type*.—Vegetative stem cuttings.
- *Time to produce a rooted young plant*.—14 to 16 days.
- *Root description*.—White and fine.
- *Rooting habit*.—Lanceolate.
- *Plant form*.—Potted and hanging plant.
- *Plant height*.—10.0 cm to 12.0 cm.
- *Plant diameter or spread*.—25.0 cm to 27.0 cm.

Lateral branches:
- *Stem*.—Solid.

*Length*.—8.0 cm to 10.0 cm.
*Diameter*.—3.0 cm to 5.0 cm.
*Number of internodes per stem*.—3 to 4.
*Internode length*.—1.0 cm.
*Node length*.—0.2 cm.
*Node diameter*.—0.2 cm.
*Texture*.—Smooth.
*Color*.—RHS N137B.

Foliage:
*Arrangement*.—Opposite.
*Length*.—4.5 cm to 5.5 cm.
*Width*.—0.7 cm to 0.9 cm.
*Shape*.—Lanceolate.
*Apex*.—Acute.
*Base*.—Obtuse.
*Margin*.—Entire.
*Texture* (*both upper and lower surfaces*).—Smooth.
*Immature leaf color*.—Upper surface: RHS 137B. Lower surface: RHS 137B.
*Mature leaf color*.—Upper surface: RHS N137A. Lower surface: RHS N137D.
*Venation pattern*.—Parallel.
*Venation color* (*both upper and lower surfaces*).—RHS N137A.

Flowers:
*Flower type and habit*.—Double, round, small spray.
*Flower position*.—Slightly above the foliage.
*Fragrance*.—Absent.
*Natural flowering season*.—Early spring to fall.
*Flower longevity on the plant*.—10 to 12 days.
*Number of flowers per spray*.—2 to 4.
*Buds*.—Length: 1.3 cm to 1.5 cm. Diameter: 0.8 cm to 1.0 cm. Shape: Ovate. Color: RHS 187A. Extrusion of the styles at bud stage: Absent.
*Corolla*.—Quantity of petals and arrangement: Greater than 30 and arranged in several whorls. Corolla height: 1.6 cm to 2.0 cm. Petal length: 4.0 cm. Petal width: 2.0 cm. Petal shape: Spoon-shaped. Petal apex: Obtuse. Petal base: Acute. Petal margin: Crenate, depth is medium. Petal texture (both upper and lower surfaces): Satiny. Petal color: Immature: Upper surface: RHS 46B. Lower surface: RHS 185B. Mature: Upper surface: RHS 46A. Lower surface: RHS 185A.
*Calyx*.—Quantity of sepals: Composed of 4 to 5 fused sepals. Calyx height: 1.4 cm to 1.6 cm. Calyx diameter (at the apex): 0.6 cm to 0.8 cm. Calyx shape: Campanulate. Sepal apex shape: Acute. Sepal texture (both upper and lower surfaces): Smooth. Sepal color: Upper surface: RHS N77A. Lower surface: RHS 137B.
*Epicalyx*.—Position of the outer lobes in relation to the calyx: Adpressed. Apex shape of inner and outer lobes: Acute. Length: 0.9 cm.

Peduncles:
*Length*.—10.0 cm to 12.0 cm.
*Diameter*.—0.2 cm.
*Strength*.—Weak.
*Texture*.—Smooth.
*Color*.—RHS N137A.

Reproductive organs:
*Stamens*.—Quantity per flower: 3 to 5. Filament length: 0.4 cm to 0.6 cm. Filament color: RHS 155A. Anther length: 0.1 cm. Anther diameter: 0.05 cm. Anther color: RHS 26D. Pollen amount: Few.
*Pistils*.—Quantity per flower: 1. Pistil length: 1.5 cm to 1.7 cm. Style length: 0.1 cm. Style color: RHS N155B. Stigma shape: Filamentous. Stigma color: RHS 187A. Ovary size: 0.7 cm to 0.9 cm. Ovary shape: Ovate. Ovary color: RHS 145A. Ovary texture: Smooth.

Fruit and seed set: No fruit and seed set observed.

Disease and pest/insect resistance: No disease and pest/insect resistance observed.

COMPARISON WITH PARENTAL LINES AND KNOWN VARIETY

'KLEDG14216' is a distinct variety of *Dianthus* and is distinguished from its parents as described in Table 1.

TABLE 1

Comparison with Parental Lines

| Characteristic | 'KLEDP14216' | Female Parent 'DCP 2006 0122' | Male Parent 'DCP 2007 0092' |
|---|---|---|---|
| Flower color | Purple and dark-red | Dark-red | Purple |
| Plant habit | Little drooping | Upright | Drooping |

'KLEDP14216' is a distinct variety of *Dianthus* and is most similar to the commercial *Dianthus* variety 'Rubin' (patent status unknown). Differences between the varieties are described in Table 2.

TABLE 2

Comparison with Similar Variety

| Characteristic | 'KLEDP14216' | 'Rubin' |
|---|---|---|
| Plant habit | Little drooping | Upright |
| Flower type | Double | Semi-double |

We claim:

1. A new and distinct variety of *Dianthus* plant designated 'KLEDP14216' as illustrated and described herein.

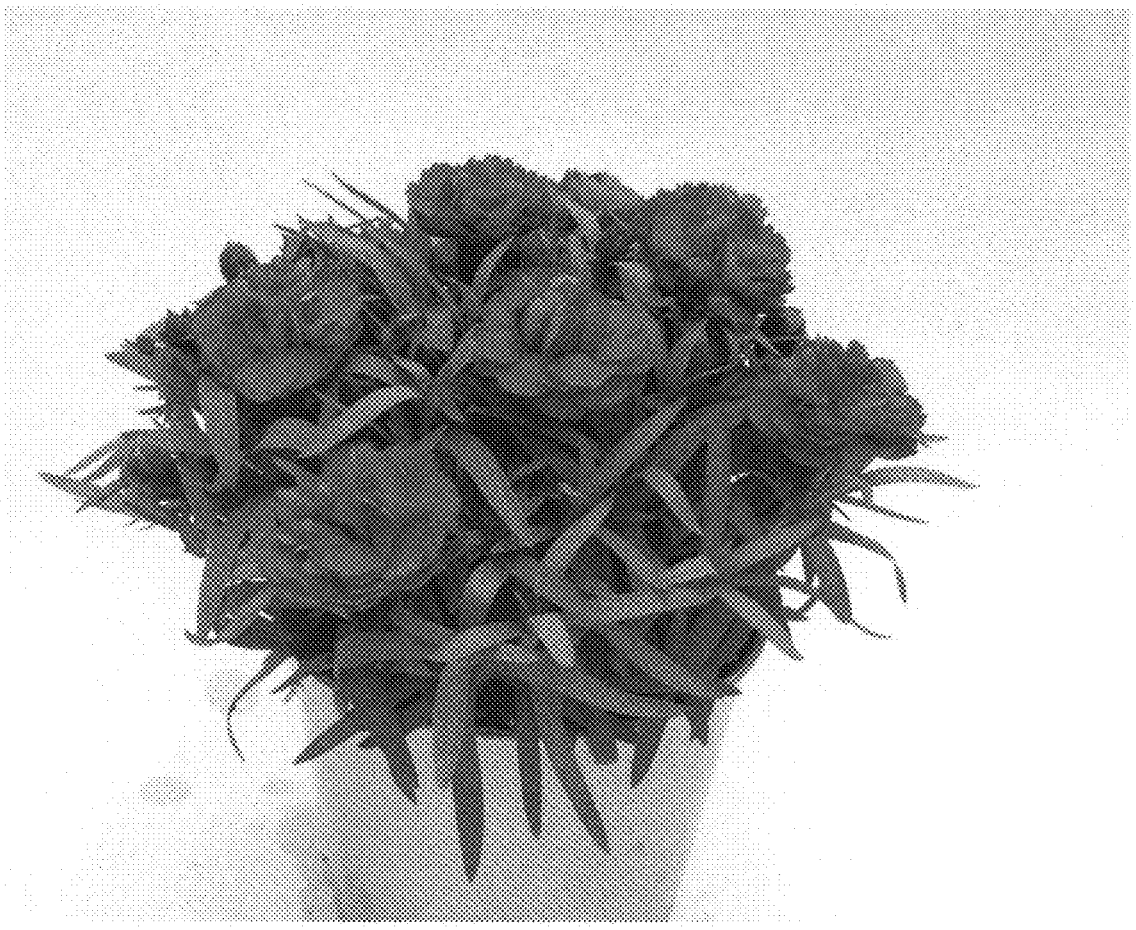

* * * * *